US 6,830,693 B2

(12) United States Patent
Govoni et al.

(10) Patent No.: US 6,830,693 B2
(45) Date of Patent: Dec. 14, 2004

(54) METHOD FOR SETTING UP A DIALYSIS TREATMENT IN A DIALYSIS MACHINE

(75) Inventors: Fabio Govoni, Renazzo (IT); Alessandro Vasta, Modena (IT)

(73) Assignee: Gambro Dasco S.p.A., Medolla (IT)

( * ) Notice: Subject to any disclaimer, the term of this patent is extended or adjusted under 35 U.S.C. 154(b) by 144 days.

(21) Appl. No.: 10/088,536

(22) PCT Filed: Jul. 20, 2001

(86) PCT No.: PCT/IB01/01305

§ 371 (c)(1),
(2), (4) Date: Jul. 22, 2002

(87) PCT Pub. No.: WO02/07797

PCT Pub. Date: Jan. 31, 2002

(65) Prior Publication Data

US 2003/0029797 A1 Feb. 13, 2003

(30) Foreign Application Priority Data

Jul. 21, 2000 (IT) .................................. T000A000727

(51) Int. Cl.$^7$ ........................... B01D 61/32; B01D 61/28
(52) U.S. Cl. ..................... 210/646; 210/85; 210/102; 210/134; 210/141; 210/143; 210/321.65; 210/321.71; 210/96.2; 210/645; 210/739; 210/929; 604/28; 604/29; 702/85
(58) Field of Search .................... 210/85, 96.2, 102, 210/134, 141, 143, 321.65, 321.71, 645, 646, 739, 929; 604/28, 29; 702/19, 85, FOR 119

(56) References Cited

U.S. PATENT DOCUMENTS

| 5,938,938 A | * | 8/1999 | Bosetto et al. .............. 210/739 |
| 2001/0004523 A1 | * | 6/2001 | Bosetto et al. ................ 435/4 |
| 2003/0073950 A1 | * | 4/2003 | Vasta et al. ................... 604/29 |

FOREIGN PATENT DOCUMENTS

| EP | 0 952 540 | 10/1999 |
| WO | WO 98/35747 | 8/1998 |

* cited by examiner

*Primary Examiner*—John Kim
(74) *Attorney, Agent, or Firm*—Finnegan, Henderson, Farabow, Garrett & Dunner, L.L.P.

(57) ABSTRACT

A method of setting up a dialysis treatment in a dialysis machine may include the steps of determining conditions of a dialysis treatment adapted to a specific patient, determining a first function (U(t)) of a first quantity (U) characterizing the dialysis treatment as a function of time (t), and determining a second function (C(t)) of a second quantity (C) characterizing the dialysis treatment. The first function (U(t)) satisfying the conditions of the dialysis treatment and corresponding to a curve having a defined shape. The second function (C(t)) is correlated with the first function (U(t)) by constants (M, N) determined experimentally and the second function (U(t)) corresponding to a curve having a shape of the same kind as the shape as the first curve.

14 Claims, 3 Drawing Sheets

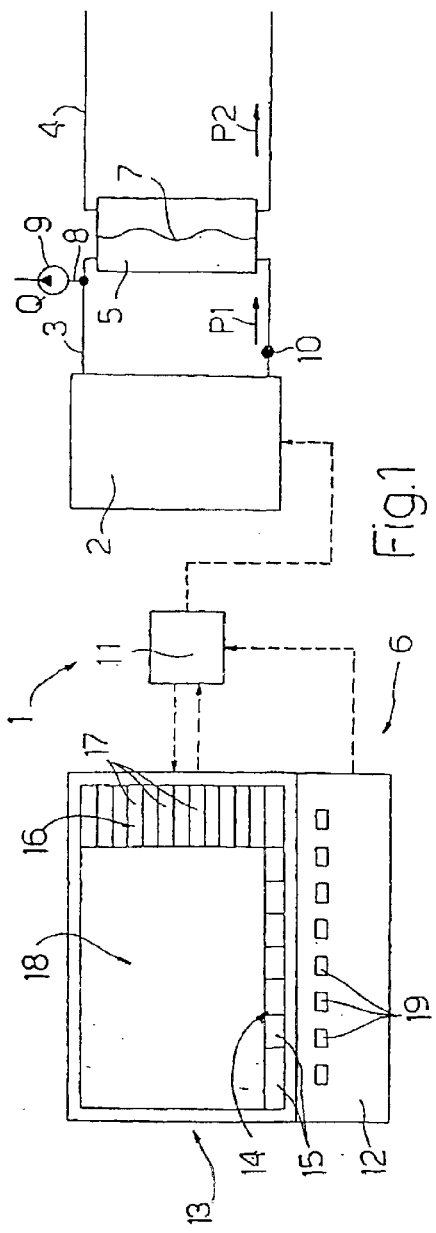
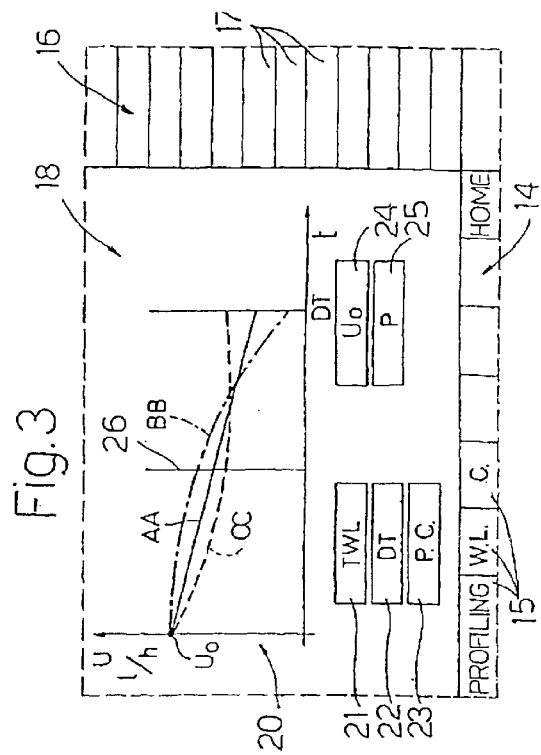
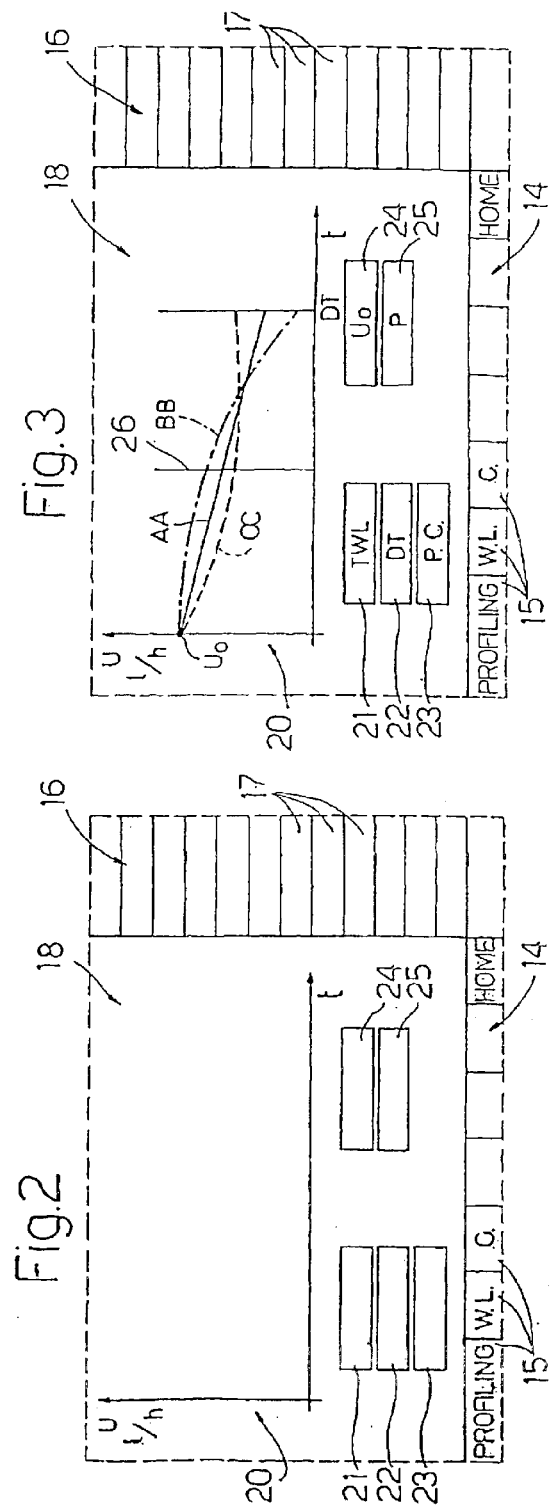

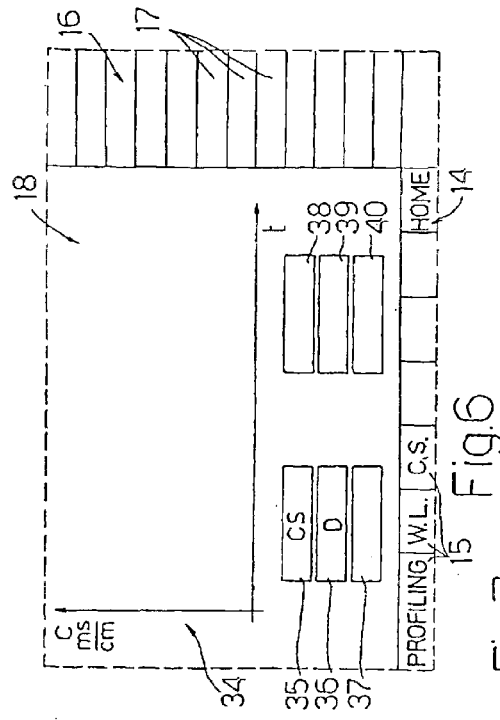
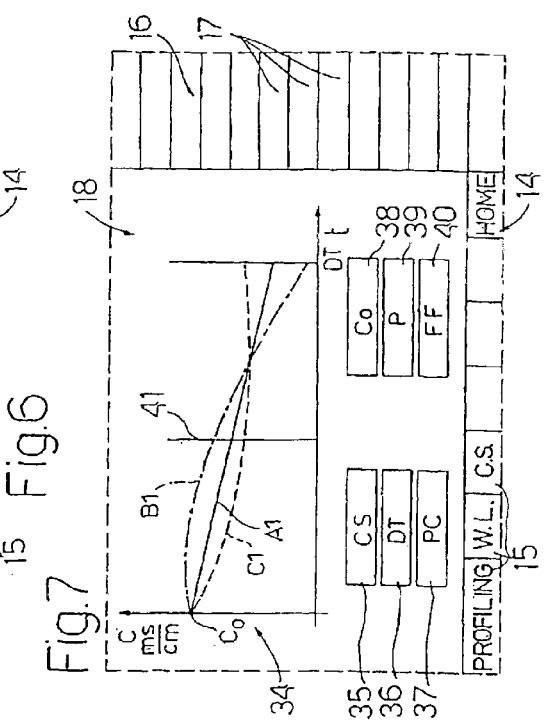

METHOD FOR SETTING UP A DIALYSIS TREATMENT IN A DIALYSIS MACHINE

The present invention relates to a method of setting up a dialysis treatment in a dialysis machine.

In general, dialysis machines are preset for carrying out dialysis treatments that are personalized for patients affected by renal insufficiency. In other words, the dialysis machines have control devices that make it possible to set up a dialysis treatment that is specific to each patient on the basis of the medical instructions. As a rule, a prescription for a patient affected by renal insufficiency and undergoing dialysis treatment comprises instructions relating to the weight loss that the patient should experience and to the amount of salts that the patient should receive in the form of ions during the dialysis treatment. Other data characterizing the dialysis treatment, such as the maximum weight loss in unit time tolerated by the patient and the duration of the dialysis treatment, can be obtained from the general conditions of health and from the patient's physical characteristics. The weight loss during a dialysis treatment is due to expulsion of a proportion of the blood fluid.

For this purpose, a dialysis machine of known type comprises an extracorporeal blood circuit connected, in use, to the patient's circulatory system, a dialysate circuit, and a filter through which the blood circuit conveys the blood fluid and the dialysate circuit conveys the dialysate. The filter comprises a semipermeable membrane, which separates, in use, the dialysate from the blood fluid and permits an exchange of ions between the dialysate and the blood fluid and the transfer of a proportion of the blood fluid through the membrane. The machine further comprises an ultrafiltration pump for expelling a defined quantity of the patient's blood fluid from the dialysate circuit and through the membrane to achieve the aforesaid weight loss. Therefore there is a biunique correspondence between the weight loss and the quantity of blood fluid expelled during the whole treatment and, similarly, between the weight loss in unit time, also called the rate of weight loss, and the delivery of the ultrafiltration pump. However, this correspondence is not valid in the case where the extracorporeal circuit is provided with an infusion bag that releases a flow of infusion fluid into the blood circuit. In this case the weight loss in unit time will be equal to the difference between the ultrafiltration flow rate and the infusion flow rate.

The extent of ion exchange is a function of the concentration of salts in the blood fluid and of the natraemia of the patient's blood fluid. In other words, the quantity of salts transferred to the patient is determined by setting the concentration of ions of the dialysate and depends on the ion concentration and on the conditions of the blood fluid. The concentration of the dialysate is measured by determining the conductivity of the dialysate and is monitored during the dialysis treatment.

In less recent dialysis machines, the values of the weight loss in unit time and of the conductivity of the dialysate were kept constant throughout the treatment and were kept relatively low owing to the fact that the patient was unable to tolerate high values, and in consequence the dialysis treatments were extremely long.

The newer dialysis machines are provided with devices for setting up the treatment, in which the values of the weight loss in unit time and of the concentration of salts in the dialysate are set in such a way that they vary as a function of time. This innovation in the field of dialysis machines occurred as a result of research in which it was found that a high weight loss in unit time can be tolerated well by an average patient in the initial stage of treatment, whereas the critical stage with regard to the weight loss in unit time is the final stage of treatment, during which the patient has already lost a large part of the weight, in the form of blood fluid, and is able to tolerate a weight loss in unit time that is relatively low compared with the initial weight loss in unit time. Furthermore, research has also shown that the patient's receptiveness to the administration of salts in the form of ions is greater in the final stage of treatment compared with the patient's receptiveness in the initial stage of the treatment. Thus, the data setting devices of the newest machines have adapted to the innovations introduced by medical research and make it possible to define both the function of the weight loss in unit time as a function of time, and the function of the conductivity of the solution of dialysate as a function of time.

Existing devices for setting up a dialysis treatment are based on various methods, some of which envisage the introduction of data on weight loss in unit time for a series of successive intervals of time of the treatment, so that a histogram is substantially defined. In the same way, conductivity data are introduced for a series of time intervals so as to define a histogram. Determination of a histogram makes it possible to define the parameters of the dialysis treatment with increasing precision as the time intervals become shorter, so that the dialysis treatment can be tailored very accurately to the requirements of a given patient. However, these methods require the input of a value for each bar of the histogram, and for this reason it takes a relatively long time to set up the dialysis treatment.

Other less refined methods envisage the setting of only the initial values and final values of weight loss in unit time and of the conductivity of the dialysate solution and the duration of the dialysis treatment and constantly varying the weight loss in unit time and the conductivity between the initial value and the final value. The setting-up time is much shorter for these methods, but they do not permit the setting up of optimum treatments for each patient.

The aim of the present invention is to provide a method of setting up a dialysis treatment in a dialysis machine that does not have the disadvantages of the prior art and, in particular, is accurate, increases the efficiency of the treatment and at the same time can be implemented easily and quickly.

According to the present invention, a method is provided for setting up a dialysis treatment in a dialysis machine comprising the steps of:

determining the conditions ($U_0$, TWL, DT) of a dialysis treatment adapted to a specific patient;

determining a first function (U(t)) of a first quantity (U) characterizing the dialysis treatment as a function of time (t), the first function (U(t)) satisfying the conditions ($U_0$, TWL, DT) of the dialysis treatment and corresponding to a curve having a defined shape;

determining a second function (C(t)) of a second quantity (C) characterizing the dialysis treatment, the second function (C(t)) being correlated with the first function (U(t)) by constants (M, N) determined experimentally and the second function (U(t)) corresponding to a curve having a shape of the same kind as the shape as the first curve.

According to the present invention, once the function of the first quantity has been set, the function of the second quantity is determined automatically, greatly reducing the time for setting up the dialysis treatment.

The present invention will now be described with reference to the accompanying drawings, which illustrate one non-limitative embodiment thereof, in which:

FIG. 1 is a schematic view of a dialysis machine constructed according to the present invention;

FIGS. 2 to 7 are images displayed by a screen of the dialysis machine of FIG. 1 during setting up of a dialysis treatment.

Figure 8:
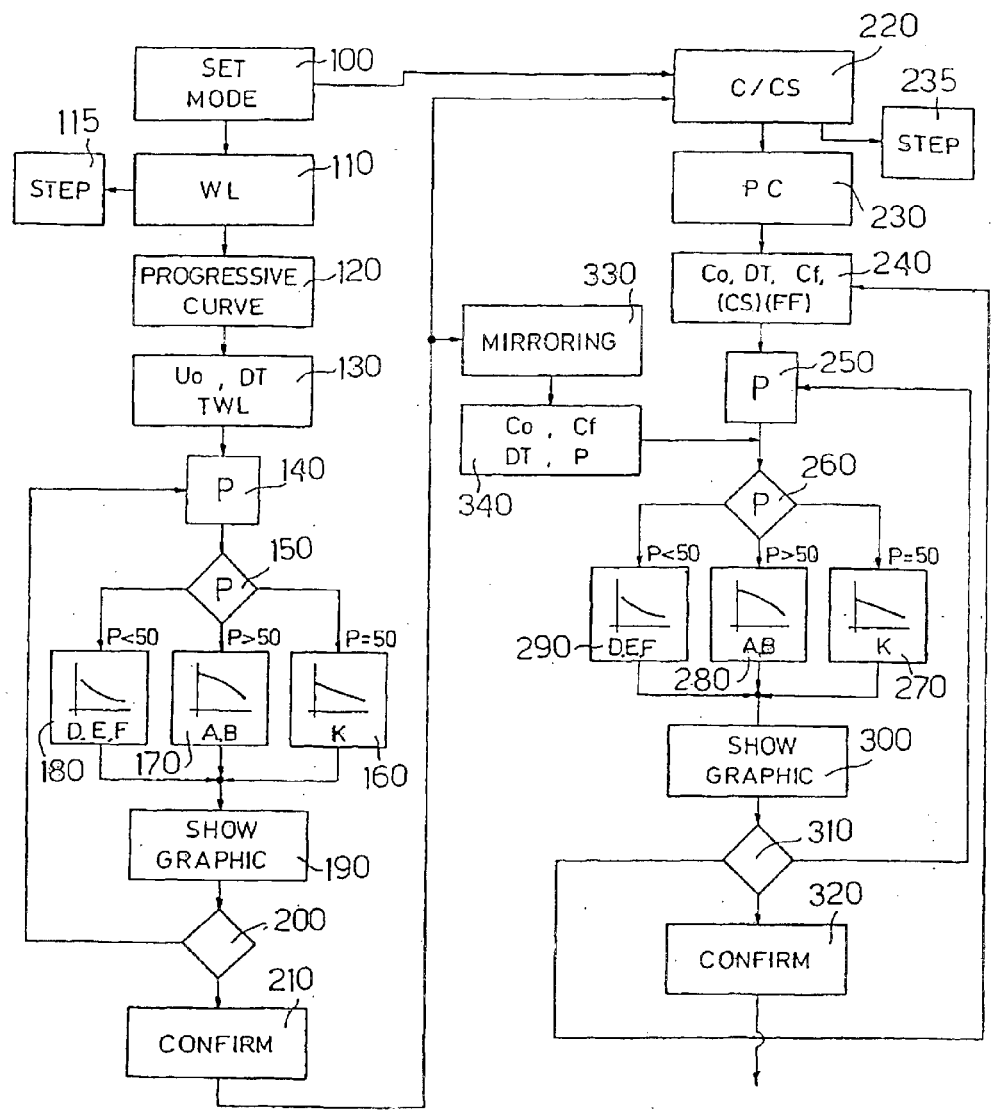
FIG. 8 is a block diagram, showing the operating modes of the machine of FIG. 1 in the stage of setting up of a dialysis treatment.

Referring to FIG. 1, reference 1 indicates the whole dialysis machine for providing dialysis treatments for patients affected by renal insufficiency. Machine 1 comprises apparatus 2 for preparing the dialysate, a dialysate circuit 3, a blood circuit 4, a filter 5 and a device 6 for setting up the dialysis treatment. Dialysate circuit 3 transports the dialysate along a path P1 through filter 5 and is connected to apparatus 2, whereas the blood circuit 4, in use, is connected to the circulatory system of a patient and conveys the blood fluid along a path P2 through filter 5, in which the dialysate fluid and the blood fluid are separated by a semipermeable membrane 7, across which the ions of the dialysate fluid are transferred to the blood fluid, whereas the impurities contained in the blood fluid are transferred to the dialysate. The degree of exchange depends on the ion concentration of the dialysate and on the natraemia of the patient's blood fluid. Along circuit 3, downstream from filter 5, there is a branch 8 for extraction of blood fluid and an ultrafiltration pump 9 for extracting a flow rate Q of blood fluid, which passes through filter 5. In practice, ultrafiltration pump 9 provides extraction of the part of the blood fluid that crosses the semipermeable membrane 7, and in this way produces the patient's weight loss. Apparatus 2 provides supply of the concentration of salts in the form of ions to the dialysate, whereas a sensor 10 mounted on dialysate circuit 3 detects the electrical conductivity C of the dialysate, the electrical conductivity C being correlated to the concentration of ions in the dialysate. Apparatus 2 and ultrafiltration pump 9 are controlled by a control unit (not shown), which determines the variation of the concentration of salts and of the delivery Q of the ultrafiltration pump 9.

Device 6 comprises a microprocessor 11, a keyboard 12 and a screen 13, which is interactive, of the "touch screen" type, and is subdivided into a zone 14, in which there are touch keys 15 for navigating and for selecting the pages of an electronic notebook, a zone 16, with touch keys 17 for controlling apparatus 2, and a zone 18 for displaying the values for setting up the dialysis treatment and the characteristic curves of the dialysis treatment. Keyboard 12 includes hard keys 19, which include a key 19 for going into a SET MODE for setting up the dialysis treatment, a key 19 "+/−" for changing the values of the data for setting up the dialysis treatment, and a key 19 for confirming the data.

On selecting key 19 for access to the SET MODE, keys 15 appear, indicating PROFILING, "WL", i.e. the option for setting the weight loss, and "C", i.e. setting of conductivity. Two keys 17 permit selection of the modes "PC" (PROGRESSIVE CURVE) and "STEP" (histogram), which permit access respectively to the mode for selection of a curve of variation of the rate of weight loss as a function of time without discontinuities in the first derivative and to a mode for setting a histogram, of a known type, of variation of the rate of weight loss as a function of time. Selection of key 17 "PC" supplies the image illustrated in FIG. 2 and includes a Cartesian system 20, which shows time t on the ordinate and, on the abscissa, the hourly weight loss U expressed in kg/h, a box/touch key 21 for input of the figure for total weight loss TWL, a box/touch key 22 for input of the dialysis time DT, a box 23 for displaying that operation is in progressive curve mode, a box/touch key 24 for input of the initial value of weight loss in unit time, i.e. the maximum weight loss $U_0$ and a box/touch key 25 for input of a parameter P, which characterizes the shape of the progressive curve. In use, the operator touches box/key 21, which becomes activated, and by means of key 19 "+/−" alters a predefined value of the total weight loss TWL until box/key 21 displays the value of the total weight loss TWL defined by the therapy, and the operator confirms that value by means of confirmation key 19. In a similar manner, by using boxes/touch keys 22 and 24 and keys 19, the operator inputs and confirms the values of DT and of $U_0$, respectively.

Once the operator has selected the "progressive curve" mode, microprocessor 11 makes reference to a group of predefined functions U(t, P) characterizing the weight loss in unit time and parametrized with parameter P. The group of functions U(t,P) comprises a family of straight lines AA, a family of parabolas BB with their convexity pointing upwards, and a family of hyperbolas CC with their convexity pointing downwards. As an example, below are given the families of functions U(t,P) that reflect the shapes of curves AA, BB and CC respectively.

Functions U(t;P) with a straight-line relationship corresponding to the family of straight lines AA $$U = K \cdot t + U_0;$$

functions U(t,P) with a course with convexity upwards corresponding to the family of parabolas BB $$U = A \cdot t^2 + B \cdot t + U_0;$$

functions U(t,P) with a course with convexity downwards corresponding to the family of hyperbolas CC $$U = \frac{D}{E + F \cdot t + t^2}$$

The progressive curve AA, BB, CC that is to be preselected corresponds to a function U(t) of the group stated above and depends on the value assigned to the discriminating parameter P, which indicates the curvature of the curve relating the value $U_0$ of the initial weight loss to a value of the final weight loss $U_f$ for t=DT, and the value of the intermediate weight loss $U_i$ for t=DT/2 according to the following relation:

$$U_i = U_f + P \cdot \frac{U_0 - U_f}{100}$$

in which P is expressed as a percentage and $U_f$ is an unknown and is always less than $U_0$, representing the maximum weight loss tolerated by the patient. In other words, the intermediate value $U_i$ of the weight loss is determined by parameter P.

Although the value of $U_f$ is unknown, the value of P equal to fifty percent indicates that the curve belongs to the family of straight lines AA, and microprocessor 11 calculates the value of K, imposing the following condition:

$$TWL = \int_0^{DT} (K \cdot t + U_0) \cdot dt$$

This condition means that the total weight loss is equal to the area subtended by a straight line belonging to the family of straight lines AA for determining coefficient K. Once the value of coefficient K is known, microprocessor 11 calculates the values of the flow U as a function of t and displays the straight line in the system of Cartesian axes 20 as shown in FIG. 3.

Parameter P is variable over a range of variability between twenty and eighty percent and for values of P greater than fifty percent the curve belongs to the family of parabolas BB, whereas for values of P less than fifty percent the curve belongs to the family of hyperbolas CC. This range of variability also requires that the value of $U_i$ is always between the value $U_0$ and the value $U_f$.

Microprocessor 11 determines the coefficients A and B of the parabola for each value of P between fifty percent and eighty percent, imposing the following conditions:

$$U_i = A \cdot (^{DT}/_2)^2 + B \cdot DT/2 + U_0 \text{ for } t=DT/2;$$

$$U_f = A \cdot DT^2 + B \cdot DT + U_0 \text{ for } t=DT;$$

$$U_i = U_f + P \cdot \frac{U_0 - U_f}{100} \text{ for } 50 < P < 80;$$

$$TWL = \int_0^{DT} (A \cdot t^2 + B \cdot t + C) \cdot dt.$$

In the four-equation system, the values DT, TWL, $U_0$ and P are known, whereas the unknowns are $U_f$, $U_i$, A and B, which vary as coefficient P varies.

Substantially similarly, the coefficients D, E, and F of the hyperbola are determined by microprocessor 11 for each value of parameter P between fifty percent and 20 percent with the following system of equations:

$$U_0 = D/E \text{ for } t=0;$$

$$U_i = \frac{D}{E + F \cdot \frac{DT}{2} + \left(\frac{DT}{2}\right)^2} \text{ for } t = \frac{DT}{2};$$

$$U_f = \frac{D}{E + F \cdot DT + DT^2} \text{ for } t = DT;$$

$$U_i = U_f + P \cdot \frac{U_0 - U_f}{100} \text{ for } 20 < P < 50;$$

$$TWL = \int_0^{DT} \left(\frac{D}{E + F \cdot t + t^2}\right) \cdot dt.$$

In the five-equation system, the values DT, TWL, $U_0$ and P are known, whereas the unknowns are $U_f$, $U_i$, D, E and F, which vary with variation of coefficient P.

In practice, once we have predefined the group of functions U(t;,P):

$$U = K \cdot t + U_0; \quad U = A \cdot t^2 + B \cdot t + U_0; \quad U = \frac{D}{E + F \cdot t + t^2}$$

the imposing of boundary conditions TWL, $U_0$, and DT selects a subset of the group of functions U(t,P) whereas assignment of a defined value to parameter P isolates a single function U(t) from the subset, so that the systems of equations become defined.

From the operational standpoint, once the values TWL, $U_0$ and DT have been assigned, the operator varies parameter P by touching the box/touch key 25 and key 19 "+/−" and microprocessor 11 displays, on screen 13, the curve corresponding to the value assigned to parameter P and displayed in the respective box/key 25. Referring to FIG. 3, each curve displayed satisfies the values TWL, $U_0$, and DT established on the basis of the doctor's prescription, therefore from the quantitative standpoint the therapeutic values are satisfied. The operator can select the qualitative course of administration for each patient by visually selecting the curve that belongs to one of the families AA, BB, CC and is best suited to the characteristics of the given patient by varying parameter P. Together with the system of Cartesian axes 20, a bar 26 is displayed, which is parallel to the ordinate, is positioned to correspond to the value DT/2, and intercepts the curve at point $U_i$.

The course of the concentration C(t) of the dialysate as a function of time is determined similarly. In this case, screen 13 supplies the image of FIG. 4 which shows a cartesian system 27, which has an abscissa showing the scale for time t and an ordinate showing the scale for conductivity C expressed in mS/cm (millisiemens per centimeter), a box/touch key 28 for input of the initial and maximum conductivity $C_0$, a box/touch key 29 for input of the final conductivity $C_f$, a box 30 for displaying the progressive curve mode, a box/touch key 31 for inputting the dialysis time DT and a box/touch key 32 for inputting parameter P.

With variation of parameter P, the progressive curve belongs to a family of straight lines A1 for P equal to fifty percent, to a family of parabolas B1 with convexity upwards for P for a value greater than fifty percent, and to a family of hyperbolas C1 for a value of P less than fifty percent.

Functions C(t) with a straight-line course corresponding to the family of straight lines A1 for P equal to 50% are as follows:

$$C = K \cdot t + C_0;$$

functions C(t) corresponding to the family of curves B1 are as follows:

$$C = A \cdot t^2 + B \cdot t + C_0;$$

functions C(t) corresponding to the family of curves C1 are as follows:

$$C = \frac{D}{E + F \cdot t + t^2}.$$

In this case there is a change in boundary conditions for determining the unknowns. With regard to the straight line it is stipulated that $$C_f = KDT + C_0 \text{ for } t=DT;$$

in which the unknown is K, whereas $C_f$, DT and $C_0$ are known.

For a value of P greater than fifty percent the curve belongs to the family of parabolas B1 and the following conditions are imposed:

$$C_i = A \cdot (^{DT}/_2)^2 + B \cdot ^{DT}/_2 + C_0 \text{ for } t=DT/2;$$

$$C_f = A \cdot DT^2 + B \cdot DT + C_0 \text{ for } t=DT;$$

$$C_i = U_f + P \cdot \frac{C_0 - C_f}{100} \text{ for } 50 < P < 80$$

In the three-equation system, A, B and $C_i$ are unknowns and $C_0$, $C_f$, DT and P are known and are entered by the operator.

For a value of P less than fifty percent the curve belongs to the family C1 and the following conditions are imposed:

$$C_0 = D/E \text{ for } t=0;$$

$$C_i = \frac{D}{E + F \cdot \frac{DT}{2} + \left(\frac{DT}{2}\right)^2} \text{ for } t = \frac{DT}{2};$$

-continued $$C_f = \frac{D}{E + F \cdot DT + DT^2} \text{ for } t = DT;$$

$$C_i = C_f + P \cdot \frac{C_0 - C_f}{100} \text{ for } 20 < P < 50.$$

In the four-equation system, D, F, F and $C_i$ are unknowns and $C_0$, $C_f$, DT and P are known and are entered by the operator.

In a similar manner to the preceding case, for each parameter P an image is supplied for the respective curve belonging to one of the families A1, B1 and C1 as illustrated in FIG. 5. All the curves that are displayed satisfy the conditions imposed by the operator, who can select the curve visually that is the most suitable for the patient undergoing the dialysis treatment.

According to the variant in FIGS. 6 and 7, the submenu activated by selecting "SET MODE" offers the options "WL" and "CS", which replaces the "C" mode and provides for stipulating the total quantity of salts that must be transferred to the patient. Selection of option "CS" determines display of the image of FIG. 6, which shows a Cartesian system 34 that has an abscissa for plotting the time t, and an ordinate for plotting the electrical conductivity C, a box/touch key 35 for input of data relating to the quantity of salts CS to be transferred to the patient, a box/touch key 36 for entering the dialysis time DT, a box 37 for displaying the progressive curve mode, a box/touch key 38 for entering the initial and maximum conductivity $C_0$, box/touch key 39 for entering discriminating parameter P and a box/touch key 40 for input of a function FF.

Function FF is an absorption function based on algorithms of a known type that make reference to the characteristics of filter 5 and to the equivalent conductivity that is determined on the basis of the general characteristics of a given patient, for whom the dialysis treatment is required.

With variation of parameter P, the curves are for example represented by the curves A1, B1 and C1.

In the case when P is equal to fifty percent, the curve belongs to family A1 and the conditions imposed are as follows:

$$C_i = C_f + \frac{C_0 - C_f}{2};$$

$$C_i = \frac{K \cdot DT}{2} + C_0;$$

$$CS = \int_0^{DT} FF(t) \cdot (K \cdot t + C_0) dt.$$

In the case when P is between fifty and eighty percent, the curve belongs to the family of curve B1 and the conditions imposed are as follows:

$$C_i = A \cdot (DT/2)^2 + B \cdot DT/2 + C_0 \text{ for } t = DT/2;$$

$$C_f = A \cdot DT^2 + B \cdot DT + C_0 \text{ for } t = DT;$$

$$C_i = U_f + P \cdot \frac{C_0 - C_f}{100} \text{ for } 50 < P < 80$$

$$CS = \int_0^{DT} FF(t) \cdot (A \cdot t^2 + B \cdot t + C) \cdot dt$$

In the four-equation system, the unknowns are $C_f$, $C_i$, A and B, whereas P, DT, CS, $C_0$ and the function FF(t) are known.

In the case when P is between twenty percent and fifty percent, the curve belongs to the family of curves C1 and the boundary conditions are as follows:

$$C_0 = D/E \text{ for } t = 0;$$

$$C_i = \frac{D}{E + F \cdot \frac{DT}{2} + \left(\frac{DT}{2}\right)^2} \text{ for } t = \frac{DT}{2};$$

$$C_f = \frac{D}{E + F \cdot DT + DT^2} \text{ for } t = DT;$$

$$C_i = C_f + P \cdot \frac{C_0 - C_f}{100} \text{ for } 20 < P < 50;$$

$$CS = \int_0^{DT} FF(t) \cdot \left(\frac{D}{E + F \cdot t + t^2}\right) \cdot dt.$$

In the five-equation system the unknowns are $C_f$, $C_i$, D, E and F, whereas CS, P, $C_0$, DT and FF(t) are known.

Once the coefficients of the curve corresponding to the assigned value of P are known, microprocessor 11 displays the curve in FIG. 7, and the operator visually monitors the course of the curve with variation of time. On the basis of visual monitoring and the patient's characteristics, the operator alters the value of P if he considers that the course must be corrected, or confirms with hard key 19 of keyboard 12 if the course of the curve is appropriate to the characteristics of a given patient.

Also when determining the conductivity function C(t), the curve is selected from among a group of functions C(t,P) parametrized with parameter P and a subset of functions C(t,P) is selected, imposing the boundary conditions DT, $C_0$ and $C_f$ or CS, FF(t), DT and $C_0$ and, finally, function C(t) is preselected by selecting a defined value of parameter P.

According to another variant, having determined the function U(t) and the respective curve, i.e. the variation of weight loss as a function of time t, the screen shows a touch key 17, which offers the option "MIRRORING" for determining function C(t) and the respective curve, i.e. the variation of the conductivity C as a function of time using only the data that were entered in connection with determination of curve U(t) and two constants M and N, which have previously been entered in the memory of microprocessor 11.

The option "MIRRORING" imposes the condition that the difference between initial flow $U_0$ and final flow $U_f$ expressed in liters/hour is equal to the difference between the initial conductivity $C_0$ and the final conductivity $C_f$ expressed in mS/cm (millisiemens per centimeter) for a known proportionality factor N. This relation is expressed by equation NN:

$$[U_O - U_F]_{l/h} = N \cdot [C_0 - C_f]_{mS/cm}.$$

The option "MIRRORING" also stipulates that the initial flow U expressed in liters/hour is equal to the initial conductivity C expressed in mS/cm for a constant M. This relation is expressed by equation MM:

$$[U_O]_{l/h} = M \cdot [C_0]_{mS/cm}.$$

The option "MIRRORING" further envisages that curve C(t) should have the same qualitative course as curve U(t), i.e. that parameter P should be the same for both curves. Obviously the treatment time DT is the same. Therefore, the values of $C_0$ and $C_f$ can be obtained from equations NN and MM, whereas DT and P are known, and accordingly it is possible to impose the conditions for determining the coefficients of the curve in the manner described previously.

In practice, three different means have been described for determining the course of the function C(t) and of the respective curve. These different means can coexist in the device 6 for setting up the dialysis treatment.

Referring to FIG. 8, the operations of setting up the dialysis treatment are shown schematically as a block diagram. Block 100 indicates selection of key 19 "SET MODE", which gives access to the options "WL" (block 110), option "C" (CONDUCTIVITY) and CS (CONDUCTIVITY/SALT) grouped in block 220. Selection of option WL gives access to selection between the option "PROGRESSIVE CURVE" (block 120) and the option "STEP CURVE" (block 115). Selection of the option "PROGRESSIVE CURVE" gives access to block 130 for input of data $U_0$, DT and TWL and to block 140 for input/change of P. Assignment of a value of P determines that verification (block 150) of whether P is greater than, equal to or less than 50 is executed. For P equal to 50, microprocessor 11 calculates coefficient K of one of the families of straight lines AA (block 160). For P>50, microprocessor 11 calculates the coefficients A and B of a parabola of family BB (block 170) and for P less than 50, microprocessor 11 calculates the coefficients D, E and F of a hyperbola of family CC (block 180). Once the coefficients of the function corresponding to a given value of P and to a given curve have been calculated, microprocessor 11 displays the curve determined by the value assigned to P on screen 13 with reference to Cartesian system 20. Once the curve is displayed, the operator decides (block 200) whether to modify the curve by entering a new value of P (block 140) so that microprocessor 11 repeats the operations shown schematically in the blocks from 150 to 190 for displaying the curve corresponding to the new value assigned to parameter P or for confirming the curve (block 210). Changing of parameter P is repeated until the operator considers that the curve is suitable for setting up the dialysis treatment. Confirmation (block 210) is effected by means of a confirmation key (HARD KEY) 19. Once the curve corresponding to function U(t) has been confirmed, the operator has three options for defining the course of the conductivity function C(t) with variation of time t. Options C and CS have already been described and have been combined in block 220 as they only differ from one another in regard to the data that are entered by the operator. The option "MIRRORING" (block 330) prevents the input of the data as obtained from the data supplied for defining the curve of U(t) and from the constants M and N obtained experimentally. Selection of the option C/CS offers the options "PROGRESSIVE CURVE" and "STEP CURVE". Selection of "PROGRESSIVE CURVE" determines presentation of the input of data (block 240) which, in the case of option "C", are substantially $C_0$ and $C_f$, since DT is known and, in the case of option "CS", are substantially CS, $C_0$ and FF(t), since DT is known. Parameter P is entered (block 250) and compared with the discriminating value 50 (block 260) for determining the coefficients of the functions corresponding to the families of curves A1, B1 and C1. The curve of function C(t) corresponding to the value of P is displayed on screen 13 (block 300) and the operator has the option of deciding (block 310) whether to change the value of P (block 250) and whether to confirm the curve displayed (block 320) by means of a hard key 19.

Selection of the option "MIRRORING" determines calculation of $C_0$ and $C_f$ (block 340), after which calculation of the coefficients of a function C(t) corresponding to a curve belonging to the families A1, B1 and C1, display of the curve and confirmation (blocks from 260 to 320) are effected in the same way as for option C. If the curve displayed by means of the MIRRORING operations does not satisfy the operator, the curve is altered by varying the value of P (block 250) and the microprocessor repeats the operations between blocks 260 and 310.

According to another variant, if the operator considers that some values of the curve do not satisfy the therapeutic requirements he also changes the values of the initial conductivity $C_0$, final conductivity $C_f$ and quantity of salts to be transferred to the patient CS.

In other words, the "MIRRORING" operation is able to supply a curve that is acceptable in itself, or a base curve that is close to the acceptable curve and can be altered for adapting the curve to the therapeutic requirements.

In the example described, the function U(t) of weight loss in unit time corresponds in fact to the delivery Q(t) of the ultrafiltration pump 9 and setting the weight loss means setting the operation of the ultrafiltration pump during the dialysis treatment. According to another variant that is not shown, the extracorporeal circuit is provided with an infusion bag that releases a flow I of infusion fluid into the extracorporeal circuit. In this case the ultrafiltration flow Q is equal to the sum of the weight loss U in unit time and the infusion flow.

What is claimed is:

1. Method of setting up a dialysis treatment in a dialysis machine (1) comprising the steps of:

determining conditions of a dialysis treatment adapted to a specific patient;

determining a first function (U(t)) of a first quantity (U) characterizing the dialysis treatment as a function of time (t), the first function (U(t)) satisfying said conditions of the dialysis treatment and corresponding to a curve having a defined shape; and determining a second function (C(t)) of a second quantity (C) characterizing the dialysis treatment, the second function (C(t)) being correlated with the first function (U(t)) by constants (M, N) determined experimentally and the second function (C(t)) corresponding to a curve having a shape of the same kind as the shape of the first curve.

2. Method according to claim 1, wherein the dialysis machine (1) comprises:

an extracorporeal blood circuit (4) for the circulation of blood in a first compartment of a dialyzer (5) having first and second compartments separated by a semipermeable membrane (7), a dialysate circuit (3) for conveying a dialysate in the second compartment of the dialyzer (5), the dialysate having a defined concentration of salts which is correlated to the electrical conductivity (C) of the dialysate, an apparatus (2) for varying the concentration of salts in the dialysate during the dialysis treatment, and an ultrafiltration pump (9) with variable delivery (Q) for extracting plasma water from the blood circulated in the extracorporeal blood circuit (4) and causing a weight loss (TWL) during the dialysis treatment, wherein the first quantity is the weight loss (U) in unit time which is correlated to the delivery (Q) of the ultrafiltration pump (9), and the second quantity is the conductivity (C) of the dialysate.

3. Method according to claim 2, wherein the constants (M, N) comprise a first constant (M), which relates a first value ($U_0$) of the weight loss (U) in unit time at the initial moment of the dialysis treatment to a value ($C_0$) of the conductivity (C) of the dialysate at the initial moment of the dialysis treatment, and a second constant (N) that relates the difference between the first value ($U_O$) and a third value ($U_f$) of the weight loss (U) in unit time at the final moment of the dialysis treatment to the difference between the second value ($C_O$) and a fourth value ($C_f$) of the conductivity (C) of the dialysate at the final moment of the dialysis treatment, the first and third values ($U_O$, $U_f$) being known from the first function.

4. Method according to claim 3, wherein the dialysis machine (1) comprises a device (6) for setting up the dialysis treatment comprising a microprocessor (11), data input (12, 13) and a screen (13), the method comprising the steps of:

supplying a first group of functions (U(t,P)) characterizing the weight loss (U) in unit time as a function of time (t) and a variable parameter (P) that is correlated with intermediate values ($U_i$) of each function (U(t;P)) of the first group;

selecting a subset of the group of functions (U(t;P)) imposing the conditions of the dialysis treatment adapted to a specific patient;

assigning values to the parameter (P) and displaying the curves corresponding to the functions (U(t,P)) of the subset and to the respective values assigned to the parameter (P); and selecting one of the functions ((U(t,P)) of the subset on the basis of the images of the curves.

5. Method according to claim 4, wherein the conditions of the dialysis treatment comprise the total weight loss (TWL), the dialysis time (DT) and the first value relative to the weight loss ($U_O$) in unit time at the initial moment of the dialysis treatment.

6. Method according to claim 4, wherein the parameter (P) is characteristic of the curvature of each first curve correlated with a respective first function ((U(t)) of the subset, and the determination of the second function (C(t)) comprises the steps of:

supplying a second group of functions C(t,P)), determining a subset of second functions C(t,P)) that satisfy the correlation with the first function (U(t)) by means of the first and second constants (M, N) and are parameterised with the parameter (P), and supplying a second function (C(t)) having the same value of parameter (P) as the first function (U(t)).

7. Method according to claim 6, wherein each first curve is displayed relative to a Cartesian system (20) on the screen (13), the parameter (P) discriminating whether the curve is a straight line, whether the curve has its curvature oriented in one direction or whether the curve has its curvature oriented in the opposite direction, and determining the degree of curvature.

8. Method according to claim 6, comprising the step of supplying the image on the screen (13) of the second curve correlated with the said second function (C(t)).

9. Method according to claim 8, comprising the step of varying the value assigned to parameter (P) for altering the shape of the second curve and the respective second function C(t)).

10. Method according to claim 8 or claim 9, comprising the step of altering the second curve by varying the value of the initial conductivity ($C_O$).

11. Method according to claim 8 or claim 9, comprising the step of altering the second curve by varying the value of the final conductivity ($C_f$).

12. Device for setting up a dialysis treatment comprising a microprocessor, a data input and a screen, the device being able to perform a method as claimed in claim 1.

13. A machine comprising:

an apparatus for preparing a dialysate;

a dialysate circuit;

a blood circuit; and a filter connected to the apparatus and the blood circuit, and further comprising a device for setting up a dialysis treatment according to claim 12.

14. Method according to claim 10, comprising the step of altering the second curve by varying the value of the final conductivity ($C_f$).

* * * * *

UNITED STATES PATENT AND TRADEMARK OFFICE
CERTIFICATE OF CORRECTION

PATENT NO. : 6,830,693 B2
DATED : December 14, 2004
INVENTOR(S) : Govoni et al.

It is certified that error appears in the above-identified patent and that said Letters Patent is hereby corrected as shown below:

Title page,
Item [57], ABSTRACT,
Line 11, "experimentally and" should read -- experimentally, and --.
Line 12, "(U(t)) corresponding" should read -- (C(t)) corresponds --.
Line 13, "as the first" should read -- of the first --.

Column 11,
Line 38, "C(t,P))," should read -- (C(t,P)), --.
Line 39, "C(t,P))" should read -- (C(t,P)) --.

Column 12,
Line 18, "C(t))." should read -- (C(t)). --.

Signed and Sealed this

First Day of March, 2005

JON W. DUDAS
*Director of the United States Patent and Trademark Office*